United States Patent [19]

Katsuda

[11] Patent Number: 5,468,497
[45] Date of Patent: Nov. 21, 1995

[54] FUMING, HOT-VAPORIZING INSECTICIDE FOR KILLING FLIES, AND METHOD FOR KILLING FLIES WITH THE SAME

[75] Inventor: Yoshio Katsuda, Nishinomiya, Japan

[73] Assignee: Dainihon Jochugiku Co., Ltd., Osaka, Japan

[21] Appl. No.: 298,153

[22] Filed: Aug. 30, 1994

[30] Foreign Application Priority Data

| Sep. 3, 1993 | [JP] | Japan | 5-254637 |
| Sep. 10, 1993 | [JP] | Japan | 5-260344 |
| Mar. 18, 1994 | [JP] | Japan | 6-074468 |
| May 10, 1994 | [JP] | Japan | 6-120595 |

[51] Int. Cl.⁶ .................................................. A01N 25/00
[52] U.S. Cl. ........................ 424/405; 424/403; 424/406
[58] Field of Search ............................ 424/405, 406; 514/531, 461

[56] References Cited

U.S. PATENT DOCUMENTS

| 3,934,023 | 1/1976 | Okuno et al. | 424/274 |
| 4,053,629 | 10/1977 | Fanta | 424/285 |
| 4,496,586 | 1/1985 | Matsui et al. | 514/531 |
| 4,622,337 | 11/1986 | Elliott et al. | 514/461 |
| 4,968,487 | 11/1990 | Yamamoto et al. | 422/125 |

*Primary Examiner*—Thurman K. Page
*Assistant Examiner*—William E. Benston, Jr.
*Attorney, Agent, or Firm*—Nath & Associates; Gary M. Nath

[57] ABSTRACT

Disclosed is a fuming, hot-vaporizing insecticide for killing flies, which contains propargylfurylmethyl 2,2,3,3-tetramethylcyclopropanecarboxylate of the general formula I:

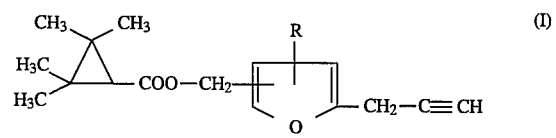

wherein R is hydrogen or methyl, as the active ingredient. The insecticide may be in any form of coil, mat or liquid. Also disclosed is a method of killing flies, using the insecticide.

36 Claims, No Drawings

FUMING, HOT-VAPORIZING INSECTICIDE FOR KILLING FLIES, AND METHOD FOR KILLING FLIES WITH THE SAME

BACKGROUND OF THE INVENTION

1. Field of the Invention

The present invention relates to a fuming, hot-vaporizing insecticide for killing flies, which contains as the active ingredient, propargylfurylmethyl 2,2,3,3-tetramethylcyclopropanecarboxylate of the general formula I:

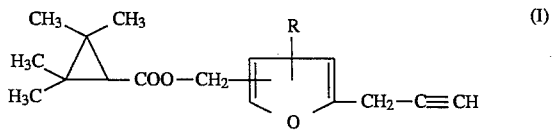

wherein R is hydrogen or methyl, and to a method for killing flies with the insecticide.

2. Prior Art

As insecticides for repelling and exterminating imaginal mosquitoes, popularly used are fuming, hot-vaporizing insecticides in the form of mosquitoes-repellent coils, electric mosquitoes-repellent mats and electric mosquitoes-repellent liquids. In these days, the breeding of mosquitoes is decreasing but there is still a great demand for such mosquito repellents. As the active ingredients in them, widely used are chrysanthemates, for example (±)-2-allyl-3-methyl-cyclopent-2-en-1-on-4-yl (+)-cis, trans-chrysanthemate (hereinafter referred to as pynaminforte), its stereoisomers such as esbiothrin and esbiol, (+)-2-propargyl-3-methyl-cyclopent-2-en-1-on-4-yl, (+)-cis,trans-chrysanthemate (hereinafter referred to as etoc), or 5-propargyl-2-furylmethyl (+)-cis, trans-chrysanthemate (hereinafter referred to as furamethrinforte).

On the other hand, some local areas such as fishing villages, factories for processing fishes and shellfishes, plants for garbage disposal, stock farming houses, chicken houses and around them are often troubled by flies more than before, though the breeding of flies is decreasing in urban areas. As the means for eradicating the sources of breeding flies, various insecticides such as emulsions, oils and powder preparations are used. In addition, space aerosols for repelling and exterminating imaginal flies are popular for domestic use, but these have a drawback that the effect thereof is often transitory and does not last long. Given the situations, a demand for space treating agents of fuming, hot-vaporizing insecticides (fuming coils, mats and liquids), of which the effect lasts for several hours or more, has become increased.

Of these, mosquitoes-repellent coils may be lighted from a match to fume in a broad space and last long, while the effect thereof is kept constant until they are burnt out. Therefore, the means of using them is an extremely reasonable insecticidal method. During its use, a mosquitoes-repellent coil releases its active ingredients therefrom at its part which is remote from the fired part thereof heated at about 800° C. by several mm and which has been heated at abut 200° to 250° C. The diffusibility of the released active ingredients is good since the smoke from the fired mosquitoes-repellent coil acts as a carrier, so that the coil displays a high insecticidal effect even in an open space. On the other hand, regarding mat-type or liquid-type mosquito repellents, the temperature of the heater (a hot plate in the mat-type or a metal ring in the liquid-type) in the heating and vaporizing device fitted in them is from 160° to 180° C. in the mat-type and from 120° to 140° C. in the liquid-type, and is lower than the temperature at the part of the coil from which its active ingredients vaporize, so that the power thereof for vaporizing their active ingredients is somewhat poor. However, these types of mosquito repellents are suitable for use in closed rooms or in the areas where smoke is not accepted.

First of all, in the process of developping a fuming, hot-vaporizing insecticide for killing flies in the form of coil, the present inventor tried to use the above-mentioned chrysanthemates that have heretofore been used in mosquitoes-repellent coil, mats and the like. However, since the effect of pynaminforte or etoc for flies was weak, it was not able to obtain a sufficient insecticidal effect even though the concentration of the active ingredient in the insecticidal preparation was increased. On the other hand, a mosquitoes-repellent coil containing furamethrinforte was shown to be effective, but needed to increase further its insecticidal effect. In addition it was disadvantageous in point of its cost. Also, in a fuming, hot-vaporizing insecticide of mat-type or liquid-type for killing flies, pynaminforte and etoc were ineffective even at high concentration, though furamethrinforte was effective at high concentration. Apart from this, the present inventor selected empenthrin which has the highest vapor pressure among commercial pyrethroids, as the active ingredient, and has already succeeded in developing a flies-repellent coil containing it. However, the coil is disadvantageous in point of its cost. In addition, since the compound vaporizes too much, a significant loss of the compound is inevitable during the drying step in producing coils containing it. In view of these facts, the flies-repellent coil was not always satisfactory. Therefore, the selection of the active ingredient which is most suitable for a fuming, hot-vaporizing insecticide for killing flies was an important theme.

Accordingly, the object of the present invention is to select an active ingredient which is most suitable for a fuming, hot-vaporizing insecticide to be used for killing flies in the form of a coil, mat or liquid and to provide a fuming, hot-vaporizing insecticide for killing flies which is excellent in all the points of insecticidal power, safety, easiness in use and producibility as well as a method of killing flies with the insecticide.

In order to solve the above-mentioned problems in the prior art, the present inventor tested fuming, hot-vaporizing insecticides containing 2,2,3,3-tetramethylcyclopropanecarboxylic acid derivative of furamethrinforte which was shown to be effective in the preceding test, the derivative hereinafter being referred to as tefuramethrin, and he admitted that tefuramethrin had a high flies-killing effect, specifically considering the fact that the vapor pressure of 2,2,3,3-tetramethylcyclopropanecarboxylates are higher than one of the corresponding chrysanthemate, and that the insecticidal activity of the former may be increased when the former is used in the form of a fuming, hot-vaporizing insecticide. The present inventor further has made an extensive scope of research, and finds that propargyl furylmethyl 2,2,3,3-tetramethylcyclopropanecarboxylate of the general formula I is specifically effective. On the basis of these findings, the inventor has completed the present invention.

That is to say, ester of (+)-2-propargyl-3-methyl-cyclopent-2-en-1-on-4-yl or 4-propargylbenzyl alcohol, which is 2,2,3,3-tetramethylcyclopropanecarboxylate has a low flies-killing effect. Therefore, now it is clear that a fuming, hot-vaporizing insecticides with a high flies-killing effect is able to be obtained by a combination of propargylfurylmethyl alcohol and 2,2,3,3-tetramethylcyclopropanecarboxylic acid.

SUMMARY OF THE INVENTION

Specifically, the present invention provides a fuming, hot-vaporizing insecticide for killing flies, characterized by containing as the active ingredient, propargylfurylmethyl 2,2,3,3-tetramethylcyclopropanecarboxylate of the general formula I:

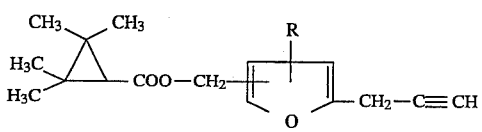

wherein R is hydrogen or methyl.

Preferred embodiments of the present invention are as follows:

A fuming, hot-vaporizing insecticidal coil for killing flies, which contains as the active ingredient the ester of the formula I in an amount of from 0.3 to 1.2%.

A fuming, hot-vaporizing insecticidal coil for killing flies, in which the active ingredient is 5-propargyl-2-furylmethyl 2,2,3,3-tetramethylcyclopropanecarboxylate.

A fuming, hot-vaporizing insecticidal coil for killing flies, in which the active ingredient is 5-propargyl-2-methyl-3-furylmethyl 2,2,3,3-tetramethylcyclopropanecarboxylate.

A fuming, hot-vaporizing insecticidal coil for killing flies, which additionally contains one or more phenol stabilizers having at least two tertiary butyl groups and having a boiling point of 250° C. or higher, in an amount of from 0.5 to 3.0 times the content of the active ingredient.

A fuming, hot-vaporizing insecticidal mat for killing flies, which contains from 30 to 150 mg of the ester of the formula I as the active ingredient, that has been infiltrated into a pulp mat having a thickness of from 1.0 to 3.0 mm and a surface area of from 7 to 15 cm² and which is heated on a hot plate in using it so as to vaporize the active ingredient therefrom.

A fuming, hot-vaporizing insecticidal mat for killing flies, in which the active ingredient is 5-propargyl-2-furylmethyl 2,2,3,3-tetramethylcyclopropanecarboxylate.

A fuming, hot-vaporizing insecticidal mat for killing flies, in which the active ingredient is 5-propargyl-2-methyl-3-furylmethyl 2,2,3,3-tetramethylcyclopropanecarboxylate.

A fuming, hot-vaporizing insecticidal mat for killing flies, which additionally contains one or more synergists for pyrethroid or esters of higher fatty acids, as the vaporization-controlling agent, in an amount of from 0.5 to 10 times the content of the active ingredient.

A fuming, hot-vaporizing insecticidal mat for killing flies, which additionally contains one or more phenol stabilizers having at least two tertiary butyl groups or hydroquinone stabilizers having at least two tertiary butyl groups, in an amount of from 0.1 to 1.0 time the content of the active ingredient.

A fuming, hot-vaporizing insecticidal liquid for killing flies, which contains as the active ingredient, the ester of the formula I in an amount of from 1 to 6% along with a solvent, the liquid being filled in a plastic bottle having therein a liquid-drawing wick, of which wick the lower part has been dipped in the liquid and the upper part is heated in using the liquid so as to vaporize the active ingredient from the liquid.

A fuming, hot-vaporizing insecticidal liquid for killing flies, in which the active ingredient is 5-propargyl-2-furylmethyl 2,2,3,3-tetramethylcyclopropanecarboxylate.

A fuming, hot-vaporizing insecticidal liquid for killing flies, in which the active ingredient is 5-propargyl-2-methyl-3-furylmethyl 2,2,3,3-tetramethylcyclopropanecarboxylate.

A fuming, hot-vaporizing insecticidal liquid for killing flies, in which the solvent is an aliphatic hydrocarbon having a boiling point of from 180° to 350° C.

A fuming, hot-vaporizing insecticidal liquid for killing flies, in which the solvent contains water.

In addition, the present invention also provides a method for killing flies, characterized in that a fuming, hot-vaporizing insecticide for killing flies, which contains as the active ingredient the ester of the formula I, is fumed or hot-vaporized under heat.

Preferred embodiments of the present invention are as follows:

A method for killing flies, wherein a fuming, hot-vaporizing insecticidal coil for killing flies, which contains as the active ingredient, the ester of the formula I in an amount of from 0.3 to 1.2%, is fumed.

A method for killing flies, wherein a fuming, hot-vaporizing insecticidal coil for killing flies, in which the active ingredient is 5-propargyl-2-furylmethyl 2,2,3,3-tetramethylcyclopropanecarboxylate.

A method for killing flies, wherein a fuming, hot-vaporizing insecticidal coil for killing flies, in which the active ingredient is 5-propargyl-2-methyl-3-furylmethyl 2,2,3,3-tetramethylcyclopropanecarboxylate.

A method for killing flies, wherein a fuming, hot-vaporizing insecticidal mat for killing flies, which contains from 30 to 150 mg of the ester of the formula I as the active ingredient, that has been infiltrated into a pulp mat having a thickness of from 1.0 to 3.0 mm and a surface area of from 7 to 15 cm², is heated on a hot plate so as to vaporize the active ingredient therefrom.

A method for killing flies, wherein a fuming, hot-vaporizing insecticidal mat for killing flies, in which the active ingredient is 5-propargyl-2-furylmethyl 2,2,3,3-tetramethylcyclopropanecarboxylate.

A method for killing flies, wherein a fuming, hot-vaporizing insecticidal mat for killing flies, in which the active ingredient is 5-propargyl-2-methyl-3-furylmethyl 2,2,3,3-tetramethylcyclopropanecarboxylate.

A method for killing flies, wherein a fuming, hot-vaporizing insecticidal liquid for killing flies, which contains as the active ingredient, the ester of the formula I in an amount of from 1 to 6% along with a solvent, the liquid being filled in a plastic bottle having therein a liquid-drawing wick, of which wick the lower part has been dipped in the liquid, is mounted on a heating and vaporizing device, and the upper part of the liquid-drawing wick is heated so as to vaporize the active ingredient from the liquid.

A method for killing flies, wherein a fuming, hot-vaporizing insecticidal liquid for killing flies, in which the active ingredient is 5-propargyl-2-furylmethyl 2,2,3,3-tetramethylcyclopropanecarboxylate.

A method for killing flies, wherein a fuming, hot-vaporizing insecticidal liquid for killing flies, in which the active ingredient is 5-propargyl-2-methyl-3-furylmethyl 2,2,3,3-tetramethylcyclopropanecarboxylate.

According to the present invention, there is provided a fuming, hot-vaporizing insecticide for killing flies, which is effective in killing not only mosquitoes but also flies because of the high flies-killing activity of the ester compound of the formula I contained therein and of the suitable vaporizability of the compound.

DETAILED DESCRIPTION OF THE INVENTION

The ester compound of the formula I can be prepared according to the conventional synthetic method of ester, by reacting 2,2,3,3-tetramethylcyclopropanecarboxylic acid or the reactive derivative thereof with the propargylfurylmethyl alcohol of the general formula II:

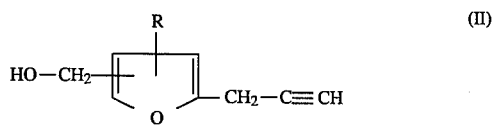

(II)

wherein R is hydrogen or methyl, or the reactive derivative thereof. Examples of the reactive derivative of the carboxylic acid are acid halides, acid anhydrides, salts with alkaline metals etc. On the other hand, examples of the reactive derivative of the alcohol are halides, etc.

The reactions may be optionally carried out in suitable solvents. Also the reactions may be carried out in the absence or presence of a deoxygenating agent or an organic or inorganic base as catalyst. The reactions may be achieved at the increased temperature. The reactions may be also carried out under an inert atmosphere.

Among the compounds of the formula I, the following ones are useful for the purpose of the invention. Of course, it is possible to use either a single compound or a mixture of two or more compounds of the formula I.

(1) Compound 1 (tefuramethrin): 5-propargyl-2-furylmethyl 2,2,3,3-tetramethylcyclopropanecarboxylate of the formula:

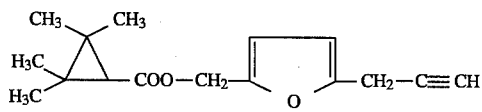

(2) Compound 2: 5-propargyl-2-methyl-3-furylmethyl 2,2,3,3-tetramethylcyclopropanecarboxylate of the formula:

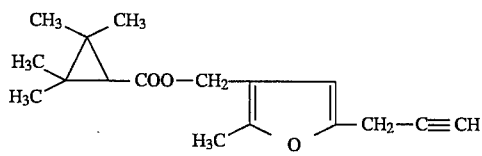

(3) Compound 3: 5-propargyl-3-furylmethyl 2,2,3,3-tetramethylcyclopropanecarboxylate of the formula:

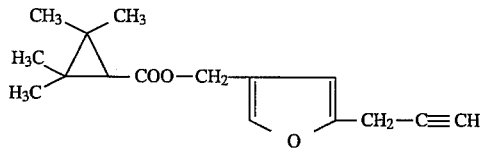

Tefuramethrin has been disclosed in Japanese Patent Publication No. Sho 46-4196, which has examples of mosquitoes-repellent coils but has no technical idea relating to fuming, hot-vaporizing insecticides for killing flies.

The insecticide of the present invention may optionally contain various conventional pyrethroids, such as pynamin, pynaminforte, bioallethrin, esbiothrin, esbiol, etoc, empenthrin, furamethrin, etc. If desired, it may further contain various synergists for pyrethroid such as piperonyl butoxide, MGK-264, Synepirin 500, S-421, lethane 384, etc. Microbicides, repellents, deodorants, aromatics, etc. may be added to the insecticide of the present invention to prepare various fuming, hot-vaporizing multi-purpose insecticides for killing flies.

The fuming, hot-vaporizing insecticidal coil of one embodiment of the present invention has a high flies-killing power and is highly vaporizable. The content of the ester of the formula I is from 0.3 to 1.2%, preferably from 0.6 to 1.2%, more preferably from 0.7 to 1.2%. When the coil is produced from the ester compound of the formula I with other active ingredients such as furamethrin or empenthrin, the total content of these active ingredients is preferably from 0.6 to 1.2%, particularly from 0.7 to 1.2%.

The coil may be produced by blending the active ingredient and other additives (in the amount from 15 to 40% of the total content) suitably chosen from among a refuse powder to be obtained by extracting pyrethrum flowers, a flaming support such as wood powder, a paste such as powder of *Machilus thunbergii*, starch, dextrin, etc., and optionally adding thereto water, a colorant, an antifungal agent, etc., and then treated the resulting mixture with the aid of an extruder, molding it into the form of coil, and drying the molded coil. Since the ester of the formula I has a lower vapor pressure than empenthrin, the loss of the former due to vaporization during the drying step in the process of producing the coil may be reduced.

According to the embodiment of the present invention, the coil may contain Compound 1 (tefuramethrin) or Compound 2 as the active ingredient, which is most useful insecticide among the compounds of the formula I, and therefore there is provided a fuming, hot-vaporizing insecticide in the form of coil, which has a high flies-killing power.

In general, pyrethroid compounds themselves including the ester compound of the formula I may be stored stably for a long period of time, when blended with dibutylhydroxytoluene of from 0 to 0.02 times the content of the active ingredient. However, the stability of the compounds in various preparations noticeably varies, depending on the kind of the active ingredient, and the kind and the amount of the stabilizer to be combined. Therefore, the stability of the active ingredients in preparations must be evaluated for each active ingredient.

The stability of the ester compound of the formula I in coils is somewhat lower than that of pynaminforte in them. However, when the ester compound of the formula I is in the insecticide according to the constitution of the present invention containing stabilizers, not only the time-dependent stability of the ester of the formula I during storage but also the stability thereof during fuming is extremely high, and the ester compound of the formula I may display a high flies-killing effect.

The present inventor investigated various kinds and amounts of stabilizers and has found that it is preferred to combine the ester compound of the formula I with one or more phenol stabilizers having at least two tertiary butyl groups and having a boiling point of 250° C. or higher in an amount of from 0.5 to 3.0 times the amount of the ester compound of the formula I, while mono-tertiary-butyl-phenol stabilizers such as 3-tertiary-butyl-4-hydroxyanisole and 2-tertiary-butyl-4-hydroxyanisole were ineffective and the effect of amine stabilizers such as N,N'-diphenyl-p-phenylenediamine and phenyl-β-naphthylamine was low. The reason why the stabilizers having a boiling point of 250° C. or higher are effective is considered because the active ingredient the ester of the formula I vaporizes at a temperature of abut 200° to 250° C. so that the stabilizers themselves are needed not to vaporize at such temperatures.

Examples of the stabilizers usable in the present invention are mentioned below, which, however, are not limitative.

(1) 2,6-Di-tertiary-butyl-4-methylphenol (BHT) [Stabilizer A]

(2) 2,2'-Methylenebis(4-methyl-6-tertiary-butylphenol) [Stabilizer B]

(3) 2,2'-Methylenebis(4-ethyl-6-tertiary-butylphenol) [Stabilizer C]

(4) 4,4'-Butylidenebis(3-methyl-6-tertiary-butylphenol) [Stabilizer D]

(5) 4,4'-Thiobis(3-methyl-6-tertiary-butylphenol) [Stabilizer E]

(6) 2-Tertiary-butyl-6-(3-tertiary-butyl-2-hydroxy-5-methylbenzyl)-4-methylphenyl acrylate [Stabilizer F]

(7) 2,4-Di-Tertiary-butylphenyl 3,5-di-tertiary-butyl-4-hydroxybenzoate [Stabilizer G]

One or more of the above-mentioned stabilizers are added to the ester of the formula I in an amount of from 0.5 to 3.0 times the Mount of the ester of the formula I. Needless-to-say, other various conventional stabilizers such as phosphites, amines and organic sulfur compounds may further be added thereto.

As another embodiment of the present invention, there is provided a fuming, hot-vaporizing insecticidal mat for killing flies, which has a high flies-killing power. The content of the ester compound of the formula I as the active ingredient is from 30 to 150 mg per mat, preferably from 40 to 150 mg per mat. This may contain, in addition to the active ingredient, various ordinary additives of vaporization-controlling agents, stabilizers, fragrant agents, dyes, etc. This may be produced by ordinary methods. Since the ester of the formula I is more vaporizable than pynaminforte and etoc, it is unnecessary to thin the mat of the present invention containing the ester of the formula I, and the thickness of the mat may be determined freely.

According to the embodiment of the present invention, the mat may contain Compound 1 (tefuramethrin) or Compound 2 as the active ingredient which is a useful insecticide among the compounds of the formula I, and therefore there is provided a fuming, hot-vaporizing insecticide in the form of mat, which has a high flies-killing power.

According to the embodiment of the present invention, the mat may contain one or more synergists for pyrethroid or esters of higher fatty acids as the vaporization-controlling agent, and therefore it may stably display the flies-killing effect from the start of using it to the end thereof.

Examples of usable synergists for pyrethroid include N-(2-ethylhexyl)-1-isopropyl-4-methyl-bicyclo[2.2.2]oct-5-ene-2,3-dicarboximide (Synepirin 500), N-(2-ethylhexyl)-bicyclo[2.2.1] hept-5-ene-2,3-dicarboximide (MGK-264), piperonyl butoxide, etc. Examples of usable esters of higher fatty acids include butyl stearate, isopropyl myristate, etc. However, these are not limitative.

Where the mat of the present invention contains stabilizer(s), the time-dependent stability of the active ingredient and the dye contained therein during storage as well as the stability thereof during heating and vaporizing the mat may be enhanced.

The dye is incorporated into the insecticide of the present invention in order to know the amount of the ingredient remained in the insecticide in use. Therefore, it is needed not to decolor during storage or use of the insecticide. As the phenol stabilizers having at least two tertiary butyl groups, preferred are those mentioned above. As usable hydroquinone stabilizers having at least two tertiary butyl groups, for example, mentioned are di-tertiary-butylhydroquinones such as 2,5-di-tertiary-butyl-hydroquinone [Stabilizer H].

The fuming, hot-vaporizing insecticide for killing flies of the present invention may be in the form of a liquid, which does not clog the liquid-drawing wick for a long period of time (30 to 60 days) and displays the excellent flies-killing activity. The content of the ester compound of the formula I as the active ingredient is from 1 to 6%, preferably from 2 to 6%. The insecticidal liquid of the present invention contains the active ingredient and a solvent and optionally contains other additives such as fragrant agents, vaporization-controlling agents, stabilizers, etc. As the vaporization-controlling agents and stabilizers, those mentioned above may be used.

The plastic bottles into which the liquid is filled and the liquid-drawing wicks to be used in the present invention are not specifically defined. For example, usable are liquid-drawing wicks formed by solidifying inorganic materials with pastes, those formed by burning them, as well as those composed of knitted fabrics of felt, cotton or unwoven fabric, or glass, inorganic fibers, plastics, woods, porous ceramics or porous vaporizable layer, and these are preferably coated with a support of glass, inorganic fibers or plastics.

According to the embodiment of the present invention, the liquid may contain as the active ingredient Compound 1 (tefuramethrin) or Compound 2 which is a useful insecticide among the compounds of the formula I, and therefore there is provided a fuming, hot-vaporizing insecticide in the form of liquid, which has a high flies-killing power.

Where the solvents are used at temperatures falling within the range of their boiling point, the active ingredient may well be heated and vaporized to display a high flies-killing power while it smells little and is toxicologically safe. In particular, aliphatic hydrocarbons such as n-paraffins, isoparaffins and naphthene compounds are preferred as the solvents.

Where water is used as the solvent, it is free from the danger of fire. In this case, water is combined with various nonionic surfactants, preferably solubilizers of polyoxyalkylene alkyl ethers. ("Solubilizers" indicate those capable of stabilizing the active ingredient in water in a clear condition, irrespective of their ability of forming micelles, and include ordinary surfactants and solvents compatible with both water and oils.)

According to the method of killing flies of the present invention, the fuming, hot-vaporizing insecticide for killing flies, which contains the ester of the formula I, is fumed or hot-vaporized under heat to display a high flies-killing activity.

Where the fuming, hot-vaporizing insecticidal coil for killing flies of the present invention, which contains the ester of the formula I as the active ingredient, is fumed according to the method of the invention, the coil may efficiently release and diffuse the active ingredient therefrom and its flies-killing activity is extremely high. Therefore, the method is extremely effective in killing flies even in a broad space.

According to the embodiment of the present invention, the coil may contain as the active ingredient Compound 1 (tefuramethrin) or Compound 2 which is a useful insecticide among the compounds of the formula I, and therefore there is provided a method of killing in the form of coil, which has the excellent effectiveness in killing flies.

Where the fuming, hot-vaporizing insecticidal mat for killing flies of the present invention, which contains the ester of the formula I as the active ingredient, is hot-vaporized under heat according to the method of the invention, it is effective in killing flies in closed rooms or in the areas where smoke is not accepted. In general, the mat is heated on the center of hot plate at 160° to 180° C.

According to the embodiment of the present invention, the mat may contain as the active ingredient Compound 1

(tefuramethrin) or Compound 2 which is a useful insecticide among the compounds of the formula I, and therefore there is provided a method of killing in the form of mat, which has the excellent effectiveness in killing flies.

Where the fuming, hot-vaporizing insecticidal liquid for killing flies of the present invention, which contains the ester of the formula I as the active ingredient, is hot-vaporized under heat according to the method of the invention, it is effective in killing flies in closed rooms or in the areas where smoke is not accepted, for a long period of time (30 to 60 days).

In general, the liquid is filled in a heating and vaporizing device having therein a liquid-drawing wick, and the device is heated so that the metal ring which surrounds the surface of the upper part of the wick may be heated at 120° to 140° C. to thereby vaporize the active ingredient from the liquid. The structure and the mode of the heating and vaporizing device to be used in the present invention are not specifically defined, and any popular one may be used freely.

According to the embodiment of the present invention, the liquid may contain as the active ingredient Compound 1 (tefuramethrin) or Compound 2 which is a useful insecticide among the compounds of the formula I, and therefore there is provided a method of killing in the form of liquid, which has the excellent effectiveness in killing flies.

Next, the present invention will be explained in more detail by means of the following examples and test examples, by which, however, the present invention is not restricted. Various changes and modifications of the illustrated embodiments can be made therein without departing from the spirit and scope of the invention.

EXAMPLE 1

0.7 parts of tefuramethrin, 0.7 parts of Stabilizer A (2,6-di-tertiary-butyl-4-methylphenol) and 98.6 parts of coil bases such as refuse powder to be obtained by extracting pyrethrum flowers, wood powder and starch were uniformly blended, kneaded the blend after adding water, extruded it and cut it into fuming, hot-vaporizing insecticidal coils for killing flies. One coil (13 g) was fumed in a six-mat room (abut 10 $m^2$), and the percentage of the active ingredient vaporized was measured to be 75%. While it was fumed for 7.5 hours in the room, all the flies and mosquitoes therein were repelled or killed.

EXAMPLE 2

80 mg of Compound 2 (5-propargyl-2-methyl-3-furylmethyl 2,2,3,3-tetramethylcyclopropanecarboxylate), 100 mg of Synepirin 500, 10 mg of Stabilizer H (2,5-di-tertiary-butylhydroquinone) and 0.6 mg of a dye of diisopropylaminoanthraquinone were infiltrated into a pulp mat having a thickness of 2.8 mm, a length of 22 mm and a width of 35 mm, to obtain a fuming, hot-vaporizing insecticidal mat for killing flies. This mat was packed in an aluminium film bag and stored at room temperature for 3 years. The bag was opened and the mat was taken out therefrom, and the mat was mounted on the hot plate (in the center part at about 170° C.) in a heating and vaporizing device and used in a closed room. This was effective against not only mosquitoes but also flies for a period of 12 hours. With the lapse of time of using it, the dye was faded in an ordinary manner. The stability of both Compound 2 and the dye during storage was good.

EXAMPLE 3

45 ml of an n-paraffin solution containing 5% of tefuramethrin was filled in a 50 ml-plastic bottle, and a liquid-drawing wick (outer diameter 7.0 mm, length 75.5 mm) provided with a holder was inserted thereinto. As the liquid-drawing wick, used was a bundle of polyester fibers covered with a knitted fabric made of polyester fibers and coated with a silicone varnish. The upper surface of the wick was heat-sealed. The n-paraffin used had a boiling point of from 250° to 280° C. The fuming, hot-vaporizing insecticidal liquid for killing flies, thus obtained, was mounted on a heating and vaporizing device, to which an electric current was applied so that the metal ring which surrounds the surface of the top of the liquid-drawing wick might be heated at 130° C. The amount of the liquid vaporized under heat was about 1.5 ml/day (used for 12 days in one day) for 30 days. During the period, the wick was not clogged, and the liquid maintained a high flies-killing activity.

Test Example 1

According to Example 1, fuming, hot-vaporizing insecticidal coil samples for killing flies were prepared, each having the formulation shown in Table 1. The time-dependent stability of these (when stored at 25° C. for 2 years) and the insecticidal activity thereof for killing imaginal flies according to the cylindrical method mentioned below were tested. The coil samples contained, in addition to the ingredients shown in Table 1, 28% by weight of starch, 0.2% by weight of sodium dehydroacetate, 25% by weight of refuse powder obtained by extracting pyrethrum flowers, and a balance of wood powder to make 100% by weight in total. The time-dependent stability of these samples was evaluated on the basis of the criteria mentioned below. The flies-killing activity thereof was represented by a relative value based on the knockdown activity (1.0) of a standard coil sample containing 1.0% by weight of empenthrin. Stabilizers A, B, C and F used in this test are those mentioned hereinabove.

Criteria for Time-dependent Stability:

o: The recovery of the active ingredient after stored for 2 years at 25° was more than 95%.

Δ: The recovery of the active ingredient after stored for 2 years at 25° C. was from 90 to 95%.

×: The recovery of the active ingredient after stored for 2 years at 25° C. was less than 90%.

Cylindrical Method:

A plastic cylinder having an inner diameter of 20 cm and a height of 43 cm was placed on a table having a height of 30 cm. The cylinder had glass disks through rubber gaskets at the top and at the bottom thereof, and the glass disk at the bottom had a hole of 5 cm diameter in the center. About 20 flies were allowed to fly in the cylinder, while was entered a coil lighted at one end from the hole of the disk at the bottom, and fumed for two minutes. After fuming, the number of the knockdown flies was counted with the lapse of time, and the $KT_{50}$ value was calculated.

TABLE 1

|  |  | Formulation (wt. %) |  |  | Time-dependent | | Loss of Active |
|---|---|---|---|---|---|---|---|
|  |  | Active Ingredients | | | Stability | | ingredients |
|  |  | Compound of the Formula I | Other Ingredient | Stabilizer | during Storage | Flies-killing Activity | during Production |
| Samples of the Invention | 1 | Tefuramethrin 0.6 | — | A 0.9 | ○ | 1.0 | Negligible |
|  | 2 | Tefuramethrin 0.7 | — | A 1.0 | ○ | 1.1 | Negligible |
|  | 3 | Tefuramethrin 0.8 | — | — | △ | 0.8 | Negligible |
|  | 4 | Tefuramethrin 0.8 | — | A 0.3 | △ | 0.9 | Negligible |
|  | 5 | Tefuramethrin 0.8 | — | A 0.5 | ○ | 1.3 | Negligible |
|  | 6 | Tefuramethrin 0.8 | — | A 1.2 | ○ | 1.3 | Negligible |
|  | 7 | Tefuramethrin 0.8 | — | A 2.0 | ○ | 1.3 | Negligible |
|  | 8 | Tefuramethrin 0.8 | — | A 2.7 | ○ | 1.2 | Negligible |
|  | 9 | Tefuramethrin 1.2 | — | A 1.2 | ○ | 1.4 | Negligible |
|  | 10 | Compound 2 0.6 | — | A 0.9 | ○ | 1.0 | Negligible |
|  | 11 | Compound 2 0.7 | — | A 1.0 | ○ | 1.1 | Negligible |
|  | 12 | Compound 2 0.8 | — | A 0.3 | △ | 0.9 | Negligible |
|  | 13 | Compound 2 0.8 | — | A 1.2 | ○ | 1.3 | Negligible |
|  | 14 | Compound 2 0.8 | — | A 2.4 | ○ | 1.3 | Negligible |
|  | 15 | Compound 2 1.2 | — | A 1.2 | ○ | 1.4 | Negligible |
|  | 16 | Compound 3 0.6 | — | A 0.9 | ○ | 1.0 | Negligible |
|  | 17 | Compound 3 0.7 | — | A 1.0 | ○ | 1.0 | Negligible |
|  | 18 | Compound 3 0.8 | — | A 0.3 | △ | 0.8 | Negligible |
|  | 19 | Compound 3 0.8 | — | A 1.2 | ○ | 1.2 | Negligible |
|  | 20 | Compound 3 1.2 | — | A 1.2 | ○ | 1.3 | Negligible |
|  | 21 | Tefuramethrin 0.3 | Furamethrin[1] 0.4 | C 0.25 F 0.45 | ○ | 1.1 | Negligible |
|  | 22 | Tefuramethrin 0.3 | Empenthrin 0.3 | A 0.4 B 0.3 | ○ | 1.0 | Slight |
| Control Samples | 1 | — | Pynaminforte 0.8 | — | ○ | 0.5 | Negligible |
|  | 2 | — | Pynaminforte 0.8 | A 0.4 | ○ | 0.5 | Negligible |
|  | 3 | — | Compound 4[2] 0.8 | A 0.4 | ○ | 0.5 | Negligible |
|  | 4 | — | Compound 5[3] 0.8 | A 0.4 | ○ | 0.4 | Negligible |
|  | 5 | — | Empenthrin 1.0 | A 0.2 | ○ | 1.0 | Large |

[1] Furamethrin: Its acid moiety is d-trans form.
[2] Compound 4: (+)-2-propargyl-3-methyl-cyclopent-2-en-1-on-4-yl 2,2,3,3-tetramethylcyclopropanecarboxylate.
[3] Compound 5: 4-propargylbenzyl 2,2,3,3-tetramethylcyclopropanecarboxylate.

The test results verify the following facts: The fuming, hot-vaporizing insecticidal coil samples for killing flies, which contained tefuramethrin, Compound 2 or Compound 3, had a higher flies-killing activity than the control pynaminforte-containing coil samples. By adding phenol stabilizers having at least two tertiary butyl groups to the samples in an amount of 0.5 times or more the amount of the ester of the formula I, the time-dependent stability of the ester of the formula I in the samples was improved so that the flies-killing effect of the samples being fumed was increased. Coils containing 0.3% of pynaminforte were effective against mosquitoes, while those containing 0.8% of pynaminforte were poorly effective against flies. The stabilizer incorporated into the pynaminforte-containing coils was almost ineffective in stabilizing the pynaminforte therein. Further, 2,2,3,3-tetramethylcyclopropanecarboxylate in which the alcohol is (+)-2-propargyl-3-methyl-cyclopent- 2-en-1-on-4-yl or 4-propargylbenzyl alcohol had a low flies-killing effect. As opposed to these, it was preferred to incorporate particular stabilizer(s) to coils containing the ester compound of the formula I, and the coils containing such stabilizer(s) had a higher flies-killing activity. Accordingly, the practical utility of these coils is extremely high. The control empenthrin-containing coil was too much vaporizable, and the loss of the active ingredient during the drying step in the process of producing it was disadvantageously large. However, the time-dependent stability of the coil during storage was good.

Test Example 2

According to Example 2, fuming, hot-vaporizing insecticidal mat samples for killing flies were prepared, each having the formulation shown in Table 2. Using a heating and vaporizing device where the temperature of the center part of the hot plate was about 168° C., the flies-killing activity of these samples was evaluated according to the continuous aeration method mentioned below. The results obtained are shown in Table 2. Meanwhile, the time dependent stability was evaluated according to the criteria in Test Example 1, and the flies-killing activity was represented by a relative value based on the knockdown effect (1.0) of a standard coil sample containing 1.0% by weight of empenthrin.

Continuous Aeration Method:

Two plastic cylinders each having an inner diameter of 20 cm and a height of 43 cm were placed one upon another, and a cylinder having an inner diameter of 20 cm and a height of 20 cm and having therein a 16-mesh wire gauze to partition its inner space into two (flies are put in the upper space thus partitioned) was placed on the upper plastic cylinder. In addition, another cylinder having the same diameter and a height of 20 cm was placed on the third cylinder. The four-stage cylinder kit was mounted on a table, while the heating and vaporizing device having therein the mat sample was set in the center of the table. In this way, the mat was heated and vaporized. About 20 flies were allowed to fly in the upper cylinder, whereupon the number of the knockdown flies was counted with the lapse of time. Twenty minutes after the exposure of the flies to the vapor from the mat, all the flies were transferred into a clean polyethylene container, and 3% aqueous sugar solution was applied thereto. After 24 hours, the number of the killed flies was counted, from which the percentage of the killed flies was obtained.

TABLE 2

| | | Formulation (mg/mat) | | | | | Time dependent Stability during Storage | Flies-killing Activity[1] | |
|---|---|---|---|---|---|---|---|---|---|
| | | Active Ingredients | | | | | | | |
| | | Compound of the Formula I | | Other Ingredient | | Vaporization-controlling Agent | Stabilizer | After One Hour | After Six Hours |
| Samples of the Invention | 1 | Tefuramethrin | 30 | — | | Synepirin 500 100 | H 10 | ○ | 1.0 (95) | 0.6 (70) |
| | 2 | Tefuramethrin | 40 | — | | Synepirin 500 100 | H 10 | ○ | 1.0 (100) | 0.7 (75) |
| | 3 | Compound 2 | 40 | — | | Synepirin 500 100 | H 10 | ○ | 1.0 (100) | 0.7 (75) |
| | 4 | Tefuramethrin | 60 | — | | Synepirin 500 100 | H 10 | ○ | 1.1 (100) | 0.8 (80) |
| | 5 | Tefuramethrin | 80 | — | | — | — | △ | 1.4 (100) | 0.6 (75) |
| | 6 | Tefuramethrin | 80 | — | | — | H 10 | ○ | 1.4 (100) | 0.7 (75) |
| | 7 | Tefuramethrin | 80 | — | | Synepirin 500 40 | H 10 | ○ | 1.3 (100) | 0.8 (85) |
| | 8 | Tefuramethrin | 80 | — | | Synepirin 500 100 | H 10 | ○ | 1.1 (100) | 0.9 (85) |
| | 9 | Tefuramethrin | 80 | — | | Synepirin 500 600 | H 10 | ○ | 1.1 (100) | 1.0 (95) |
| | 10 | Tefuramethrin | 80 | — | | Synepirin 500 100 | — | △ | 1.1 (100) | 0.8 (85) |
| | 11 | Tefuramethrin | 80 | — | | Synepirin 500 100 | A 40 | ○ | 1.1 (100) | 0.9 (90) |
| | 12 | Tefuramethrin | 80 | — | | Synepirin 500 100 | A 80 | ○ | 1.1 (100) | 0.9 (90) |
| | 13 | Tefuramethrin | 150 | — | | Synepirin 500 100 | H 15 | ○ | 1.3 (100) | 1.0 (95) |
| | 14 | Compound 2 | 60 | — | | Synepirin 500 100 | H 10 | ○ | 1.1 (100) | 0.8 (80) |
| | 15 | Compound 2 | 80 | — | | — | — | △ | 1.4 (100) | 0.6 (75) |
| | 16 | Compound 2 | 80 | — | | — | H 10 | ○ | 1.4 (100) | 0.7 (75) |
| | 17 | Compound 2 | 80 | — | | Synepirin 500 100 | — | △ | 1.1 (100) | 0.8 (85) |
| | 18 | Compound 2 | 80 | — | | Synepirin 500 100 | H 10 | ○ | 1.1 (100) | 0.9 (85) |
| | 19 | Compound 2 | 150 | — | | Synepirin 500 100 | H 15 | ○ | 1.3 (100) | 0.9 (95) |
| | 20 | Compound 3 | 60 | — | | Isopropyl Myristate 100 | H 10 | ○ | 1.1 (100) | 0.7 (80) |
| | 21 | Compound 3 | 80 | — | | — | — | △ | 1.4 (100) | 0.6 (70) |
| | 22 | COmpound 3 | 80 | — | | — | H 10 | ○ | 1.4 (100) | 0.7 (75) |
| | 23 | Compound 3 | 80 | — | | Synepirin 500 100 | — | △ | 1.0 (100) | 0.7 (80) |
| | 24 | Compound 3 | 80 | — | | Synepirin 500 100 | H 10 | ○ | 1.1 (100) | 0.8 (90) |
| | 25 | Compound 3 | 150 | — | | Isopropyl Myristate 100 | H 15 | ○ | 1.2 (100) | 0.8 (90) |
| | 26 | Tefuramethrin Compound 2 | 40 40 | — | | Synepirin 500 100 | H 10 | ○ | 1.1 (100) | 0.9 (90) |
| Control Samples | 1 | — | | Pynaminforte | 60 | Isopropyl Myristate 10 | A 40 | ○ | 0.4 (65) | 0.5 (70) |
| | 2 | — | | Pynaminforte | 150 | Isopropyl Myristate 15 | A 40 | ○ | 0.5 (70) | 0.5 (75) |
| | 3 | — | | Etoc | 60 | Isopropyl Myristate 35 | A 40 | ○ | 0.5 (75) | 0.5 (75) |
| | 4 | — | | Etoc | 150 | Isopropyl Myristate 80 | A 40 | ○ | 0.5 (75) | 0.5 (75) |
| | 5 | — | | Compound 6[2] | 80 | Synepirin 500 100 | A 40 | ○ | 0.5 (75) | 0.5 (75) |

[1] Flies-killing Activity: This means a relative value based on the knockdown effect (1.0) of a standard coil sample containing 1.0% by weight of empenthrin. The parenthesized value indicates the percentage of the killed flies.
[2] Compound 6: (±)-2-allyl-3-methyl-cyclopent-2-en-1-on-4-yl 2,2,3,3-tetramethylcyclopropanecarboxylate.

The test results verify the following facts: The fuming, hot-vaporizing insecticidal mat samples for killing flies, which contained tefuramethrin, Compound 2 or Compound 3 which is the ester compound of the formula I, had a higher knockdown activity and a higher flies-killing activity than the control pynaminforte-containing or etoc-containing mat samples. Mats containing from 10 mg to 40 mg of pynaminforte or etoc were effective against mosquitoes, while those containing 150 mg of the active ingredient (pynaminforte or etoc) were ineffective against flies. Practical use of the latter is difficult. In particular, the knockdown effect of the latter was poor. Since pynaminforte and etoc have a lower vapor pressure than the ester compound of the formula I, the increase in the content of the former in the mat does not always result in the increase in the vapor of the active ingredient to be emitted from the mat but will merely result in the increase in the amount of the non-used residue of the mat. Esters of (±)-2-allyl-3-methyl-cyclopent-2-en-1-on-4-ol which is 2,2,3,3-tetramethyl-cyclopropanecarboxylate had a low flies-killing effect. Therefore, now it is clear that a fuming, hot-vaporizing insecticides with a high flies-killing effect is able to be obtained by the ester of propargylfurylmethyl alcohol and 2,2,3,3-tetramethyl-cyclopropanecarboxylic acid. In order to increase the amount of the vapor of the control active ingredient (pynaminforte or etoc) to be emitted from the control mats, the thickness of the control mats was reduced to 1 mm (the thickness of the mats tested in this test was 2.8 mm) and these were again tested. However, the effect of these thin mats did not almost improved.

Test Example 3

According to Example 3, fuming, hot-vaporizing insecticidal liquid samples for killing flies were prepared, each having the formulation shown in Table 3. Each sample was put in a bottle set in a heating and vaporizing device. The metal ring in the device was heated to about 132° C. so that the top of the liquid-drawing wick in the bottle might be heated. The flies-killing activity of these samples was evaluated according to the continuous aeration method mentioned in Test Example 2. The results obtained are shown in Table 3.

TABLE 3

|  |  | Formulation (%) | | | | Flies-killing Activity[1] | |
| --- | --- | --- | --- | --- | --- | --- | --- |
|  |  | Active Ingredients | | | | | |
|  |  | Compound of the Formula I | | Other Ingredient | | Solvent | After One Day | After Thirty Days |
| Samples of the Invention | 1 | Tefuramethrin | 1.0 | — |  | n-Paraffin | 1.0 (90) | 0.9 (90) |
|  | 2 | Tefuramethrin | 2.0 | — |  | Water | 1.1 (95) | 1.0 (95) |
|  | 3 | Compound 2 | 2.0 | — |  | n-Paraffin | 1.1 (95) | 1.0 (90) |
|  | 4 | Tefuramethrin | 3.0 | — |  | n-Paraffin | 1.2 (98) | 1.0 (95) |
|  | 5 | Tefuramethrin | 5.0 | — |  | n-Paraffin | 1.3 (100) | 1.2 (98) |
|  | 6 | Tefuramethrin | 6.0 | — |  | n-Paraffin | 1.4 (100) | 1.3 (95) |
|  | 7 | Tefuramethrin | 3.0 | — |  | Water | 1.3 (98) | 1.1 (96) |
|  | 8 | Compound 2 | 3.0 | — |  | n-Paraffin | 1.2 (98) | 1.0 (95) |
|  | 9 | Compound 2 | 5.0 | — |  | n-Paraffin | 1.3 (100) | 1.2 (95) |
|  | 10 | Compound 2 | 3.0 | — |  | Water | 1.3 (95) | 1.5 (95) |
|  | 11 | Compound 3 | 3.0 | — |  | n-Paraffin | 1.1 (95) | 1.0 (90) |
|  | 12 | Compound 3 | 5.0 | — |  | n-Paraffin | 1.2 (95) | 1.1 (90) |
|  | 13 | Compound 3 | 3.0 | — |  | Water | 1.2 (95) | 1.1 (95) |
| Control Samples | 1 | — |  | Pynaminforte | 3.0 | n-Paraffin | 0.4 (0) | 0.3 (0) |
|  | 2 | — |  | Pynaminforte | 6.0 | n-Paraffin | 0.5 (0) | 0.4 (0) |
|  | 3 | — |  | Etoc | 3.0 | n-Paraffin | 0.8 (10) | 0.6 (10) |
|  | 4 | — |  | Etoc | 6.0 | n-Paraffin | 0.9 (10) | 0.8 (15) |

[1]Flies-killing Activity: This means a relative value based on the knockdown effect (1.0) of a standard coil sample containing 1.0% by weight of empenthrin. The parenthesized value indicates the percentage of the killed flies.

The test results verify the following facts: The fuming, hot-vaporizing insecticidal liquid samples for killing flies, which contained tefuramethrin, Compound 2 or Compound 3 which is the ester compound of the formula I, had a higher knockdown activity and a higher flies-killing activity than the control pynaminforte-containing or etoc-containing liquid samples. Liquids containing from 2.6% of pynaminforte or containing from 0.7 to 1.3% of etoc were effective against mosquitoes, while the knockdown effect of those containing 6% of the active ingredient (pynaminforte or etoc) was poor and the flies-killing effect of them was extremely low. Therefore, it was almost impossible to expect the practical use of the liquids containing pynaminforte or etoc. The increase in the concentration of pynaminforte or etoc in the liquids caused clogging of the liquid-drawing wick during use and was therefore not practicable. These facts support the practical usefulness of the fuming, hot-vaporizing insecticidal liquids for killing flies, which contain the ester of the formula I.

As has been explained in detail in the above, the fuming, hot-vaporizing insecticide for killing flies of the present invention, which contains the ester of the formula I as the active ingredient, have various advantages.

Specifically, the invention of claim 1 provides a fuming, hot-vaporizing insecticide for killing flies, which is satisfactorily effective against not only mosquitoes but also flies, which is safe and is used with ease and which is produced efficiently.

The invention of claims 2 to 4 provides a fuming, hot-vaporizing insecticidal coil for killing flies, which has a high flies-killing activity and which efficiently releases and diffuses the active ingredient therefrom.

The invention of claim 5 provides a fuming, hot-vaporizing insecticidal coil for killing flies, of which not only the time-dependent stability during storage but also the stability during fuming it has been enhanced.

The invention of claims 6 to 8 provides a fuming, hot-vaporizing insecticidal mat for killing flies, which has an excellent flies-killing activity.

The invention of claim 9 provides a fuming, hot-vaporizing insecticidal mat for killing flies, which stably maintains its flies-killing activity from the start of using it to the end thereof.

The invention of claim 10 provides a fuming, hot-vaporizing insecticidal mat for killing flies, which has an improved time-dependent stability of the active ingredient and the dye contained therein during storage and has an improved stability of itself when the mat is heated and vaporized.

The invention of claims 11 to 13 provides a fuming, hot-vaporizing insecticidal liquid for killing flies, which displays an excellent flies-killing activity for a long period of time (30 to 60 days) without causing clogging of the liquid-drawing wick used.

The invention of claim 14 provides a fuming, hot-vaporizing insecticidal liquid for killing flies, which has a high flies-killing power and which emits little odor and is therefore toxicologically safe.

The invention of claim 15 provides a fuming, hot-vaporizing insecticidal liquid for killing flies, which is free from the danger of fire.

The invention of claim 16 provides a method for killing flies, which uses the ester of the formula I as the active ingredient and is effective in killing not only mosquitoes but also flies.

The invention of claims 17 to 19 provides a method for killing flies, where a fuming, hot-vaporizing insecticidal coil for killing flies is fumed to display an excellent flies-killing activity. The vapor of the active ingredient to be generated by fuming the coil diffuses well, and the method is effective in killing flies in a broad space.

The invention of claims 20 to 22 provides a method for killing flies, where a fuming, hot-vaporizing insecticidal mat for killing flies is heated and vaporized to display an excellent flies-killing activity. The method is especially suitable for killing flies in closed rooms or in the areas where smoke is not accepted.

The invention of claims 23 to 25 provides a method for killing flies, where a fuming, hot-vaporizing insecticidal liquid for killing flies is heated and vaporized to display an excellent flies-killing activity. Since the flies-killing activity of the liquid lasts long (30 to 60 days), this method is especially suitable for killing flies in closed rooms or in the areas where smoke is not accepted, for a long period of time.

While the invention has been described in detail and with reference to specific embodiments thereof, it will be apparent to one skilled in the art that various changes and modifications can be made therein without departing from the spirit and scope thereof.

What is claimed is:

1. A fuming, hot-vaporizing insecticide for killing flies, characterized by containing as the active ingredient, propargylfurylmethyl 2,2,3,3-tetramethylcyclopropanecarboxylate of the general formula I:

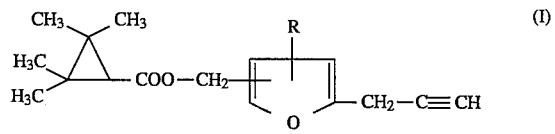

wherein R is hydrogen or methyl.

2. The fuming, hot-vaporizing insecticide for killing flies as claimed in claim 1, which is in the form of a coil containing from 0.3 to 1.2% of propargylfurylmethyl 2,2,3,3-tetramethylcyclopropanecarboxylate of the general formula I:

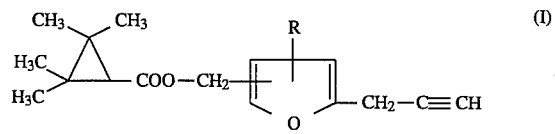

wherein R is hydrogen or methyl, as the active ingredient.

3. The fuming, hot-vaporizing insecticide for killing flies as claimed in claim 2, in which the active ingredient is 5-propargyl-2-furylmethyl 2,2,3,3-tetramethylcyclopropanecarboxylate.

4. The fuming, hot-vaporizing insecticide for killing flies as claimed in claim 2, in which the active ingredient is 5-propargyl-2-methyl-3-furylmethyl 2,2,3,3-tetramethylcyclopropanecarboxylate.

5. The fuming, hot-vaporizing insecticide for killing flies as claimed in claim 2, which additionally contains one or more phenol stabilizers having at least two tertiary butyl groups and having a boiling point of 250° C. or higher, in an amount of from 0.5 to 3.0 times the content of the active ingredient.

6. The fuming, hot-vaporizing insecticide for killing flies as claimed in claim 1, which is in the form of a mat prepared by infiltrating from 30 to 150 mg of propargylfurylmethyl 2,2,3,3-tetramethylcyclopropanecarboxylate of the general formula I:

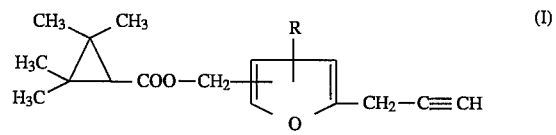

wherein R is hydrogen or methyl, as the active ingredient, into a pulp mat support having a thickness of from 1.0 to 3.0 mm and a surface area of from 7 to 15 cm² and, the mat being heated on a hot plate in using it so as to vaporize the active ingredient therefrom.

7. The fuming, hot-vaporizing insecticide for killing flies as claimed in claim 6, in which the active ingredient is 5-propargyl-2-furylmethyl 2,2,3,3-tetramethylcyclopropanecarboxylate.

8. The fuming, hot-vaporizing insecticide for killing flies as claimed in claim 6, in which the active ingredient is 5-propargyl-2-methyl-3-furylmethyl 2,2,3,3-tetramethylcyclopropanecarboxylate.

9. The fuming, hot-vaporizing insecticide for killing flies as claimed in claim 6, which additionally contains one or more synergists for pyrethroid or esters of higher fatty acids, as the vaporization-controlling agent, in an amount of from 0.5 to 10 times the content of the active ingredient.

10. The fuming, hot-vaporizing insecticide for killing flies as claimed in claim 6, which additionally contains one or more phenol stabilizers having at least two tertiary butyl groups or hydroquinone stabilizers having at least two tertiary butyl groups, in an amount of 0.1 to 1.0 time the content of the active ingredient.

11. The fuming, hot-vaporizing insecticide for killing flies as claimed in claim 1, which is in the form of a liquid containing from 1 to 6% of propargylfurylmethyl 2,2,3,3-tetramethylcyclopropanecarboxylate of the general formula I:

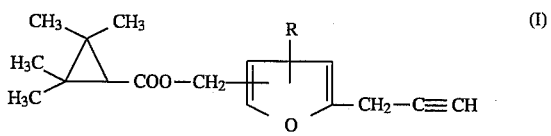

wherein R is hydrogen or methyl, as the active ingredient, along with a solvent, the liquid being filled in a plastic bottle having therein a liquid-drawing wick, of which wick the lower part has been dipped in the liquid and the upper part is heated in using the liquid so as to vaporize the active ingredient from the liquid.

12. The fuming, hot-vaporizing insecticide for killing flies as claimed in claim 11, in which the active ingredient is 5-propargyl-2-furylmethyl 2,2,3,3-tetramethylcyclopropanecarboxylate.

13. The fuming, hot-vaporizing insecticide for killing flies as claimed in claim 11, in which the active ingredient is 5-propargyl-2-methyl-3-furylmethyl 2,2,3,3-tetramethylcyclopropanecarboxylate.

14. The fuming, hot-vaporizing insecticide for killing flies as claimed in claim 11, in which the solvent is an aliphatic hydrocarbon having a boiling point of from 180° to 350° C.

15. The fuming, hot-vaporizing insecticide for killing flies as claimed in claims 11, in which the solvent contains water.

16. A method for killing flies, characterized in that a fuming, hot-vaporizing insecticide for killing flies, which contains propargylfurylmethyl 2,2,3,3-tetramethylcyclopropanecarboxylate of the general formula I:

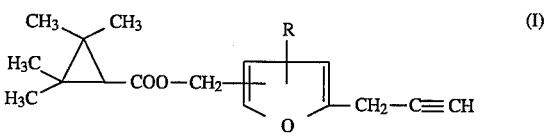

wherein R is hydrogen or methyl, as the active ingredient, is fumed or hot-vaporized under heat.

17. The method for killing flies as claimed in claim 16, wherein a fuming, hot-vaporizing insecticidal coil for killing flies, which contains from 0.3 to 1.2% of propargylfurylmethyl 2,2,3,3-tetramethylcyclopropanecarboxylate of the general formula I:

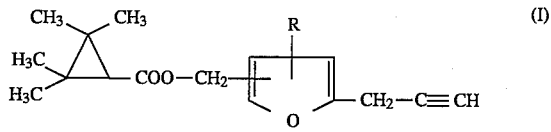

wherein R is hydrogen or methyl, as the active ingredient, is fumed.

18. The method for killing flies as claimed in claim 17, in which the active ingredient is 5-propargyl-2-furylmethyl 2,2,3,3-tetramethylcyclopropanecarboxylate.

19. The method for killing flies as claimed in claim 17, in which the active ingredient is 5-propargyl-2-methyl-3-furylmethyl 2,2,3,3-tetramethylcyclopropanecarboxylate.

20. The method for killing flies as claimed in claim 16, wherein a fuming, hot-vaporizing insecticidal mat for killing flies, which contains from 30 to 150 mg of propargylfurylmethyl 2,2,3,3-tetramethylcyclopropanecarboxylate of the general formula I:

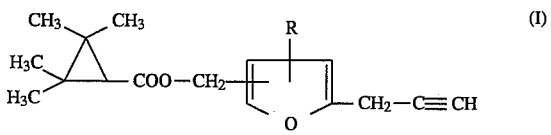

wherein R is hydrogen or methyl, as the active ingredient, that has been infiltrated into a pulp mat support having a thickness of from 10 to 3 0 mm and a surface area of from 7 to 15 cm² is heated on a hot plate so as to vaporize the active ingredient therefrom.

21. The method for killing flies as claimed in claim 20, in which the active ingredient is 5-propargyl-2-furylmethyl 2,2,3,3-tetramethylcyclopropanecarboxylate.

22. The method for killing flies as claimed in claim 20, in which the active ingredient is 5-propargyl-2-methyl-3-furylmethyl 2,2,3,3-tetramethylcyclopropanecarboxylate.

23. The method for killing flies as claimed in claim 16, wherein a fuming, hot-vaporizing insecticidal liquid for killing flies, which contains from 1 to 6% of propargylfurylmethyl 2,2,3,3-tetramethylcyclopropanecarboxylate of the general formula I:

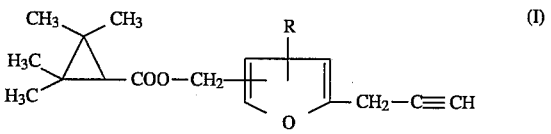

wherein R is hydrogen or methyl, as the active ingredient, along with a solvent, is filled in a plastic bottle having therein a liquid-drawing wick, of which wick the lower part has been dipped in the liquid, the bottle is mounted on a heating and vaporizing device, and the upper part of the liquid-drawing wick is heated so as to vaporize the active ingredient from the liquid.

24. The method for killing flies as claimed in claim 23, in which the active ingredient is 5-propargyl-2-furylmethyl 2,2,3,3-tetramethylcyclopropanecarboxylate.

25. The method for killing flies as claimed in claim 23, in which the active ingredient is 5-propargyl-2-methyl-3-furylmethyl 2,2,3,3-tetramethylcyclopropanecarboxylate.

26. The fuming, hot-vaporizing insecticide for killing flies as claimed in claim 3, which additionally contains one or more phenol stabilizers having at least two tertiary butyl groups and having a boiling point of 250° C. or higher, in an amount of from 0.5 to 3.0 times the content of the active ingredient.

27. The fuming, hot-vaporizing insecticide for killing flies as claimed in claim 4, which additionally contains one or more phenol stabilizers having at least two tertiary butyl groups and having a boiling point of 250° C. or higher, in an amount of from 0.5 to 3.0 times the content of the active ingredient.

28. The fuming, hot-vaporizing insecticide for killing flies as claimed in claim 7, which additionally contains one or more synergists for pyrethroid or esters of higher fatty acids, as the vaporization-controlling agent, in an amount of from 0.5 to 10 times the content of the active ingredient.

29. The fuming, hot-vaporizing insecticide for killing flies as claimed in claim 8, which additionally contains one or more synergists for pyrethroid or esters of higher fatty acids, as the vaporization-controlling agent, in an amount of from 0.5 to 10 times the content of the active ingredient.

30. The fuming, hot-vaporizing insecticide for killing flies as claimed in claim 7, which additionally contains one or more phenol stabilizers having at least two tertiary butyl groups or hydroquinone stabilizers having at least two tertiary butyl groups, in an amount of 0.1 to 1.0 time the content of the active ingredient.

31. The fuming, hot-vaporizing insecticide for killing flies as claimed in claim 8, which additionally contains one or more phenol stabilizers having at least two tertiary butyl groups or hydroquinone stabilizers having at least two tertiary butyl groups, in an amount of 0.1 to 1.0 time the content of the active ingredient.

32. The fuming, hot-vaporizing insecticide for killing flies as claimed in claim 9, which additionally contains one or more phenol stabilizers having at least two tertiary butyl groups or hydroquinone stabilizers having at least two tertiary butyl groups, in an amount of 0.1 to 1.0 time the content of the active ingredient.

33. The fuming, hot-vaporizing insecticide for killing flies as claimed in claim 12, in which the solvent is an aliphatic hydrocarbon having a boiling point of from 180° to 350° C.

34. The fuming, hot-vaporizing insecticide for killing flies as claimed in claim 13, in which the solvent is an aliphatic hydrocarbon having a boiling point of from 180° to 350° C.

35. The fuming, hot-vaporizing insecticide for killing flies as claimed in claim 12, in which the solvent contains water.

36. The fuming, hot-vaporizing insecticide for killing flies as claimed in claim 13, in which the solvent contains water.

* * * * *

UNITED STATES PATENT AND TRADEMARK OFFICE
CERTIFICATE OF CORRECTION

PATENT NO. : 5,468,497
DATED : Nov. 21, 1995
INVENTOR(S) : Yoshio Katsuda

It is certified that error appears in the above-indentified patent and that said Letters Patent is hereby corrected as shown below:

Column 20, line 31 (claim 20), correct line 31 to read as follows:

-- thickness of from 1.0 to 3.0 mm and a surface area of from --

Signed and Sealed this

Twenty-sixth Day of March, 1996

BRUCE LEHMAN

*Attest:*

*Attesting Officer*    *Commissioner of Patents and Trademarks*